(12) United States Patent
Rao et al.

(10) Patent No.: US 10,114,030 B2
(45) Date of Patent: Oct. 30, 2018

(54) DETECTION AGENT FOR DETECTING 25-HYDROXY VITAMIN D, PREPARATION METHOD AND USE

(71) Applicant: SHENZHEN NEW INDUSTRIES BIOMEDICAL ENGINEERING CO., LTD, Shenzhen (CN)

(72) Inventors: Wei Rao, Shenzhen (CN); Tinghua Li, Shenzhen (CN); Kai Du, Shenzhen (CN); Jinyun Yuan, Shenzhen (CN); Kai Luo, Shenzhen (CN); Huiling Yu, Shenzhen (CN)

(73) Assignee: SHENZHEN NEW INDUSTRIES BIOMEDICAL ENGINEERING CO., LTD, Shenzhen (CN)

( * ) Notice: Subject to any disclaimer, the term of this patent is extended or adjusted under 35 U.S.C. 154(b) by 191 days.

(21) Appl. No.: 15/309,744

(22) PCT Filed: Jul. 10, 2014

(86) PCT No.: PCT/CN2014/082003
§ 371 (c)(1),
(2) Date: Nov. 8, 2016

(87) PCT Pub. No.: WO2016/004613
PCT Pub. Date: Jan. 14, 2016

(65) Prior Publication Data
US 2017/0184615 A1    Jun. 29, 2017

(51) Int. Cl.
*G01N 33/82*  (2006.01)
*G01N 33/532*  (2006.01)
*C07K 16/44*  (2006.01)

(52) U.S. Cl.
CPC .......... *G01N 33/82* (2013.01); *G01N 33/532* (2013.01)

(58) Field of Classification Search
CPC ............................. G01N 33/82; G01N 33/532
See application file for complete search history.

(56) References Cited

U.S. PATENT DOCUMENTS

| 8,785,603 B2 * | 7/2014 | Sahakian | G01N 33/82 424/141.1 |
| 9,804,176 B2 * | 10/2017 | Wei | C07K 16/44 |
| 2013/0059825 A1 * | 3/2013 | Sahakian | G01N 33/82 514/167 |

FOREIGN PATENT DOCUMENTS

| CN | 1070509 A | 3/1993 |
| CN | 103163306 A | 6/2013 |
| CN | 103588872 A | 2/2014 |
| CN | 103857698 A | 6/2014 |
| CN | 104076155 A | 10/2014 |
| WO | 2007140962 A2 | 12/2007 |
| WO | 2009070594 A1 | 6/2009 |
| WO | 2011144661 A1 | 11/2011 |
| WO | 2012/129650 A1 | 10/2012 |

OTHER PUBLICATIONS

Extended European Search Report, dated Jan. 18, 2018, from EP Application No. 14897186.4, 7 pages.
English Translation of the International Search Report for International Application No. PCT/CN2014/082003, dated Apr. 7, 2015 (2 pages).
Li, Shuijun et al., Progress in the research of vitamin D metabolism and detecting methods for 25-hydroxyvitamin, Int. J. Lab. Med, vol. 33, No. 24, Dec. 31, 2012 (Dec. 31, 2012), pp. 3028-3030.

* cited by examiner

*Primary Examiner* — Shafiqul Hao
(74) *Attorney, Agent, or Firm* — Kagan Binder, PLLC (57) ABSTRACT

Provided are a detection agent for detecting hydroxy vitamin D, preparation method thereof, and use thereof in 25-hydroxy vitamin D immunological detection. The detection agent comprises a conjugate formed by a 25-hydroxy vitamin D antigen derivative and protein carrier, and magnetic spheres coated by the conjugate. Also provided is a 25-hydroxy vitamin D detection kit comprising the detection agent.

20 Claims, 2 Drawing Sheets

DETECTION AGENT FOR DETECTING 25-HYDROXY VITAMIN D, PREPARATION METHOD AND USE

TECHNICAL FIELD

The present disclosure relates to the field of biological immunoassay. More specifically, it relates to a detection agent for detecting 25-hydroxyvitamin D and the preparation method and use thereof.

BACKGROUND

Vitamin D is a fat-soluble vitamin. Only a small portion of the vitamin D in human body is derived from food (<10%), while 90% of the vitamin D required in vivo derives from the ultraviolet irradiation on the skin by the Sun. The primary form of vitamin D in human body is vitamin D2 (ergocalciferol) and vitamin D3 (cholecalciferol). The major nutrition sources of vitamin D2 are some vegetables, yeast, and fungi foods. Vitamin D3 is formed as a result of the conversion of subcutaneous 7-dehydrocholesterol affected by the Sun.

Vitamin D2 and vitamin D3 derived from food sources or autosynthesis enters the liver via the blood circulation and are converted to 25-OH vitamin D2 and 25-OH vitamin D3 by 25-hydroxylation enzyme, respectively, and referred to collectively as 25-OH vitamin D. The content of 25-OH vitamin D in the serum or plasma can reflect the total amount of vitamin D from food intake and autosynthesis. Therefore, 25-OH vitamin D is a best indicator of vitamin D nutritional status.

25-hydroxyvitamin D is a main storage form of vitamin D and an essential nutrient for the metabolic activity in the human body. In addition to the effect on the bones in the traditional sense, 25-OH vitamin D may also have a non-skeletal effect impact on autoimmune disease, cardiovascular disease, diabetes, cancer, and so on. Studies have found that vitamin D deficiency can directly affect the expression of human genes which are associated with many diseases such as rheumatoid arthritis, diabetes, and the like.

At present, the clinical quantitative detection of vitamin D has become a routine item in tests and physical examination. Therefore, it is particularly important to establish a fast, simple, sensitive, accurate, and reliable method of vitamin D detection. Quantitative detection of 25-hydroxyvitamin D mainly includes physical and chemical assays and immunological methods. The application of physical and chemical assays using, e.g., liquid chromatography-mass spectrometry (LC-MS) is limited due to the expensive equipment, complex sample preparation, time-consuming and tedious process, to name a few. Immunological method is sensitive, rapid, simple and specific, and thus has now become the primary vitamin D assay. A mainstream products currently on the market for the detection of 25-hydroxyvitamin D is a detection kit produced by Diasorin, Italian, the detection method of which is implemented by using ABEI (N-4-aminobutyl-N ethylisoluminol)-labelled 25-hydroxyvitamin D antigen derivatives that compete with the antigens in the sample to bind with the 25-hydroxyvitamin D antibody coated on magnetic microspheres, and then adding an excitation substrate to produce a luminescent signal, enabling quantitative detection of 25-hydroxyvitamin D. Such operating mechanism is better illustrated in FIG. 1 (the specific operation steps and experimental conditions may be found in the manual of DiaSorin-VD). In the detection process, the stability of ABEI-labeled 25-hydroxyvitamin D antigen derivatives is the most important factor affecting the stability of detection. However, 25-hydroxyvitamin D antigen derivative has poor stability, with its activity weakened when exposed to light or heat. Therefore, the reagents in the above detection kit suffers from poor stability and vulnerable activity.

Thus, the instability of the 25-hydroxyvitamin D antigen derivative used in the immunological competition assay method leads to a short storage life for immunological detection agents for 25-hydroxyvitamin D detection, which adversely affects their use and detection results. In addition, stringent storage conditions have caused great inconvenience in storage and transportation. All of these have become the bottleneck for large-scale commercialized application of such methods.

SUMMARY OF THE INVENTION

In view of the above drawbacks, one aspect of the present disclosure provides a detection agent for detecting 25-hydroxyvitamin D, which couples a 25-hydroxyvitamin D antigen derivative with a protein carrier before immobilizing the same to magnetic microspheres. Immobilization to magnetic microspheres can significantly improve the stability of the antigen derivative while the specific structure of the antigen derivative allow more accurate detection of 25-hydroxyvitamin D.

Another aspect of the present disclosure provides a process for preparing the detection agent for detecting 25-hydroxyvitamin D and a process of immunoassay for detecting 25-hydroxyvitamin D using the above detection agent. In another aspect of the disclosure, an immunoassay kit comprising the 25-hydroxyvitamin D detection agent is also provided herein.

A further aspect of the present disclosure provides a detection agent for detecting 25-hydroxyvitamin D, comprising a conjugate formed by a 25-hydroxyvitamin D antigen derivative and a protein carrier, and a magnetic sphere coated by the conjugate.

Figure 1:
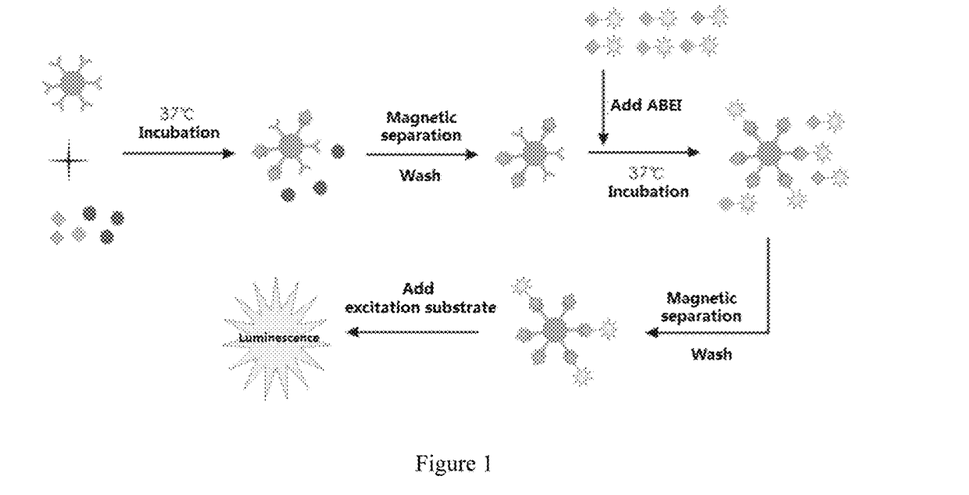
FIG. 1 shows a schematic of the detection mechanism of a 25-hydroxyvitamin D detection kit DiaSorin-VD available from Diasorin (Italy) according to its manual, wherein the referential signs are listed below.
Figure 2:
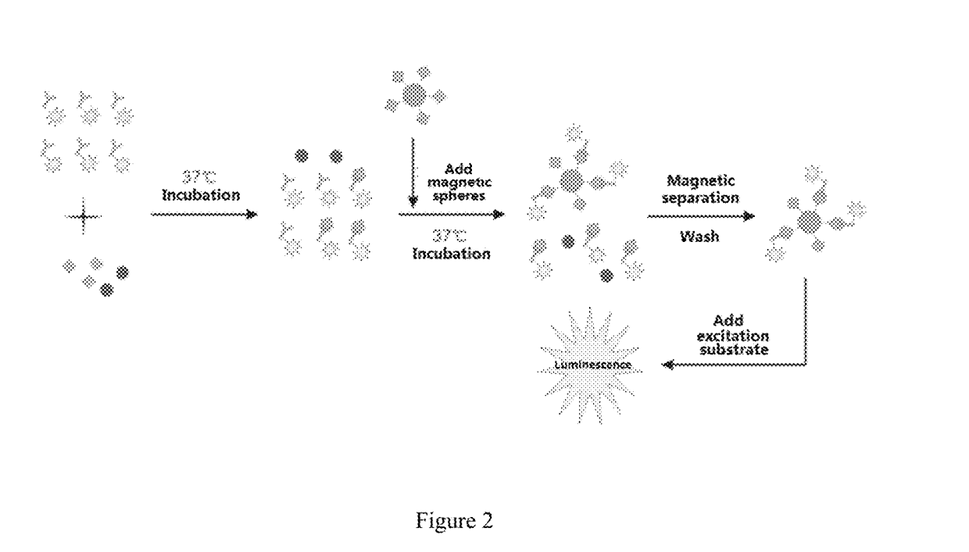
FIG. 2 shows a schematic of the detection mechanism of a 25-hydroxyvitamin D according to the present disclosure, wherein the referential signs are listed below.

In prior art, for the detection of 25-hydroxyvitamin D, a 25-hydroxyvitamin D antigen derivative is marked with a luminescent label, while a magnetic sphere is coated by a 25-hydroxyvitamin D antibody, the working mechanism of which is shown in FIG. 1. However, such product suffers from poor stability since 25-hydroxyvitamin D antigen derivatives are photosensitive and prone to be oxidized. Therefore, 25-hydroxyvitamin D antigen derivatives are easily deactivated at least partially during the luminescence labeling process. In addition, the 25-hydroxyvitamin D antigen derivative with a luminescent label also suffers from poor stability during long-term storage in solution and consequent activity decrease. Therefore, the storage conditions for such detection agent for 25-hydroxyvitamin D are stringent, which, together with the poor stability, result in short life span and poor application effect.

In the present disclosure, the 25-hydroxyvitamin D antigen derivative is coated on a solid-phase carrier, i.e., a magnetic sphere. The freedom of the 25-hydroxyvitamin D antigen derivative molecules is restricted on the one hand, and the irradiation effect on the 25-hydroxyvitamin D antigen derivative molecules is at least partially shielded by the color of the magnetic sphere on the other hand. Therefore, the stability of the 25-hydroxyvitamin D antigen derivative in solution is greatly improved, which may in turn extend the effective life span and improve the detection accuracy.

In the present disclosure, the 25-hydroxyvitamin D antigen derivative suitable for preparing the detection agents may be those commonly used in the art, such as the 25-hydroxyvitamin D antigen derivative described in the U.S. Patent Application Pub. No. 20130059825A1, the contents of which is incorporated hereby by way of reference.

In some particular embodiments, the 25-hydroxyvitamin D antigen derivative has the following formula (I):

Formula (I)

wherein m is 0, 1, 2, or 3, and n is 2, 3, 4, 5, or 6.

The 25-hydroxyvitamin D antigen derivative as shown in formula (I) is an effective agent for detecting 25-hydroxyvitamin D, which may simultaneously recognize 25-hydroxyvitamin D2 and 25-hydroxyvitamin D3. In the present disclosure, the 25-hydroxyvitamin D antigen derivative with the specific structure as shown is conjugated to a protein carrier and further used in coating a magnetic sphere, the stability thereof thus greatly improved. The inventors noticed that, such 25-hydroxyvitamin D antigen derivative has a side chain of a certain length (i.e., a connecting arm is introduced at the C22 position in the basic structure of vitamin D). For this type of antigen derivative, when coupled to a protein carrier and coating a magnetic sphere, the basic structure of vitamin D and the protein carrier are bridged by a chain of a certain length. As a result, the spatial effect is reduced, which significantly restricts the mobility of the antigen derivative molecules and reduces freedom of the antigen derivative molecules. Furthermore, the stability of the antigen derivative is greatly increased by shielding off the irradiation effect on the antigen derivative molecules with the magnetic sphere, and the impacts of storage and transportation process on the antigen derivative are also reduced, both of which help extend the effective life span. Meanwhile, since the mobility of the antigen derivative molecules is restricted and freedom of the antigen derivative molecules is reduced, the binding sites for the antibodies are more easily exposed to facilitate the binding of the antigen derivative and the antibodies. Therefore, the specificity of the binding is enhanced, rendering a more accurate detection result that is closer to the true value. The inventors further conducted comparative experiments with 25-hydroxyvitamin D antigens. That is, the 25-hydroxyvitamin D antigens are coupled to a protein carrier before used in coating magnetic spheres, and the coated magnetic spheres are used in detection of a series of samples. The result comparison with that of LC-MS on the same samples revealed that the linear correlation of the detection results obtained by these two methods are not as good as the linear correlation between the detection results obtained using the detection agents derived from the 25-hydroxyvitamin D antigen derivative according to the present disclosure and the detection results obtained using LC-MS.

A protein carrier suitable for the present disclosure may be an animal-origin or a human-origin protein, including but not limited to, bovine serum albumin (BSA), cationic bovine serum albumin (cBSA), hemocyanin (KLH), ovalbumin (OVA), serum albumin HAS, bovine γ-globulin, and human γ-globulin. The protein carriers may mediate the binding of the 25-hydroxyvitamin D antigen derivatives with the antibodies. In addition, in the present disclosure, the protein carriers may also play a role in bridging the 25-hydroxyvitamin D antigen derivatives and the magnetic spheres so that the antigen derivatives, after coupling with the protein carriers, may further bind with the magnetic spheres to form a detection agent as a whole to improve the stability of the antigen derivatives.

The magnetic spheres used herein may be hollow or solid, or porous, but not limited thereto. In the case that the magnetic spheres are porous magnetic spheres, the conjugates may also present in the pores of the magnetic spheres. The magnetic spheres used in the present disclosure preferably have a spherical shape so that the conjugates may evenly coat the magnetic spheres and non-specific adsorption may be reduced during the use of the detection agents prepared as such, allowing accurate results. In the present disclosure, the particle size of the magnetic spheres is preferably 0.5 μm-5 μm, and more preferably 0.8-3.0 μm. This range of particle size may allow good dispersion of the magnetic spheres in solution and also satisfy the requirement of immunological analysis for the particle size range of solid-phase carriers.

To form a more stable connection between the conjugate and the magnetic spheres, the magnetic spheres used in the present disclosure carry functional modification groups on their surfaces. Such functional modification groups are suitable for direct or indirect connection with the conjugate formed by 25-hydroxyvitamin D and the protein carriers. The functional modification groups include, but not limited to, one or more moieties selected from the group consisting of the following: an epoxy group, a sulfonyl group, a carboxyl group, an amino group, an aldehyde group, an amide group, a mercapto group, and a hydroxyl group. When the surface of the magnetic sphere is modified with functional groups such as a carboxyl group, an amino group, a mercapto group, a hydroxyl group and the like, the magnetic sphere may directly couple with the conjugate by condensation. If the surface of the magnetic sphere is modified with the other functional groups, further modification and activation of the magnetic sphere, e.g., by known techniques in the art, are typically necessary to obtain a functional group that may form a chemical bond with the conjugate.

The present disclosure further provides a process for preparing the detection agent for detecting 25-hydroxyvitamin D as described above, comprising coating the magnetic sphere with the conjugate formed by a 25-hydroxyvitamin D antigen derivative and a protein carrier. It should be noted that the coating process may include two schemes. One scheme is to form a conjugate of a 25-hydroxyvitamin D antigen derivative and a protein carrier and then coating the magnetic spheres. The other scheme is to carry out the coupling reaction between the 25-hydroxyvitamin D antigen derivative and the protein carrier and the coating of the magnetic spheres simultaneously.

In some particular embodiment, the process may comprise activating the magnetic sphere with a first activator before coating the magnetic bead. The activated magnetic spheres (e.g., in a concentration of 1 to 100 mg/ml) are then dispersed into a buffer solution, and the conjugate (e.g., in an amount of 1 to 20 μg per mg magnetic sphere) formed by the 25-hydroxyvitamin D antigen derivative and the protein carrier is added to react with the magnetic spheres. After the reaction, the detection agent is obtained by separating solid matter from liquid and washing the solid matter. The first activator is at least one of N,N-dicyclohexyl carbodiimide (DCC) and 1-(3-dimethylaminopropyl)-3-ethylcarbodiimide hydrochloride (EDC), or a mixture of at least one of N,N-dicyclohexyl carbodiimide and 1-(3-dimethylaminopropyl)-3-ethylcarbodiimide hydrochloride with at least one of N-hydroxysuccinimide (NHS) and N-Hydroxysulfosuccinimide sodium salt. The buffer solution used herein may include, but not limited to, carbonate buffer, phosphate buffer, borate buffer, and Tris buffer.

In some of the embodiments, the process described herein may further comprise a step of preparing the conjugate formed by a 25-hydroxyvitamin D antigen derivative and a protein carrier, which comprises allowing a 25-hydroxyvitamin D antigen derivative and a protein carrier to go through a coupling reaction at the presence of a coupling agent and a solvent to yield the conjugate. The coupling agent may be at least one selected from the group consisting of glutaraldehyde and N,N'-disuccinimidyl carbonate; and/or the solvent may be at least one selected from the group consisting of dimethylformamide, dimethylsulfoxide, acetone, and chloroform.

In yet some other embodiments, the step of preparing the conjugate formed by a 25-hydroxyvitamin D antigen derivative and a protein carrier may comprise: m) obtaining a 25-hydroxyvitamin D antigen derivative with a carboxyl group and activating the same with a second activator; and n) coupling the activated 25-hydroxyvitamin D antigen derivative with a protein carrier at the presence of a solvent and generating the conjugate by separation; wherein the second activator is a mixture of at least one of N-hydroxysuccinimide and N-hydroxysuccinimide sodium salt with at least one of N,N-dicyclohexyl carbodiimide and 1-(3-dimethylaminopropyl)-3-ethyl-carbodiimide hydrochloride; and/or, the solvent is at least one selected from the group consisting of dimethylformamide, dimethylsulfoxide, acetone, and chloroform. In a particular embodiment, in step m), the 25-hydroxyvitamin D antigen derivative is allowed to react with cyclic anhydride to introduce a carboxyl group. The cyclic anhydride may be any cyclic dianhydride, such as at least one selected from the group consisting of succinic anhydride, glutaric anhydride and diglycolic anhydride.

In a particular embodiment, the molar ratio of the 25-hydroxyvitamin D antigen derivative to the protein carrier is 10:1 to 20:1, preferably 15:1. The molar ratio chosen herein ensure a sufficient amount of antigen derivative molecules to be coupled to the protein carriers as well as effective subsequent coupling of the protein carriers to the magnetic spheres.

The disclosure herein further provides a process of immunoassay for detecting 25-hydroxyvitamin D, comprising: allowing 25-hydroxyvitamin D in a subject sample and the detection agent described above to competitively bind with a 25-hydroxyvitamin D antibody conjugated with a label. Thus the content of 25-hydroxyvitamin D in the sample is detected. Wherein, the label includes, but not limited to, a fluorescent label, a luminescent label, a biotin label, a gold label, and an enzymatic label. The means and techniques for obtaining detection parameters or indicators may differ when different labels are used, but they are all techniques known by a person skilled in the art, such as ELISA or chemiluminescent detection method.

The present disclosure further provides a process for luminescent immunoassay of 25-hydroxyvitamin D, comprising: a. incubating a subject sample with a 25-hydroxyvitamin D antibody conjugated with a luminescent label, wherein the incubation temperature may be a conventional incubation temperature, such as 4 to 40° C., while the incubation time may be 30 to 180 min; b. incorporating the mixture obtained from step a with the detection agent, so that the 25-hydroxyvitamin D in a subject sample and the detection agent competitively bind with the 25-hydroxyvitamin D antibody conjugated with a luminescent label; c. performing magnetic separation to yield a conjugate of the 25-hydroxyvitamin D antibody conjugated with a luminescent label and the detection agent; d. adding an excitation substrate to the conjugate obtained from step c to generate a luminescent signal; and e. calculating an amount of the 25-hydroxyvitamin D in the subject sample according to the intensity of the luminescent signal detected in step d. Specifically, the content of 25-hydroxyvitamin D in the sample may be determined by comparison between the luminescent signal intensity of the subject sample with a standard curve obtained from the test of a 25-hydroxyvitamin D antigen standard. The subject sample contains 25-hydroxyvitamin D, the content of which is to be determined. The luminescent label may be, for example, ABEI.

Furthermore, the present disclosure provides an immunoassay kit for detection of 25-hydroxyvitamin D, comprising a 25-hydroxyvitamin D antibody conjugated with a label and the detection agent described herein. The label includes, but not limited to, a fluorescent label, a luminescent label, a biotin label, a gold label, and an enzymatic label. In some embodiments, the kit further comprises one or more selected from the group consisting of a displacer (such as 8-aniline-1-naphthalenesulfonic acid (ANS)), a washing liquid, a vitamin D standard, a chromogenic substrate solution, and a reaction stop solution. By using the 25-hydroxyvitamin D detection agent disclosure herein, the detection kit according to the present disclosure has improved stability, extended effective life span, and more accurate detection results.

The inventors propose herein, for the first time, forming a conjugate of a 25-hydroxyvitamin D antigen derivative and a protein carrier and coating magnetic spheres with the same to obtain a 25-hydroxyvitamin D detection agent. The synergetic effect of the 25-hydroxyvitamin D antigen derivative, the protein carrier, and the solid-phase carrier, i.e., the magnetic spheres, can significantly improve the stability of the 25-hydroxyvitamin D antigen derivative and yield a detection agent with good stability. The 25-hydroxyvitamin D antigen derivative, after modification with the protein carrier and the magnetic spheres, has improved binding specificity with the antibodies. Therefore, the 25-hydroxyvitamin D detection agent according to the present disclosure may overcome the deficiencies in the prior art caused by the instability of 25-hydroxyvitamin D antigen derivatives, such as the limited life span of the associated detection kit, the instability of associated detection process, inaccurate detection results, and the like. The preparation method of 25-hydroxyvitamin D detection agent is also easy and simple. Such 25-hydroxyvitamin D detection agent according to the present disclosure may be used in the preparation of highly stable, accurate, and universal 25-hydroxyvitamin D detection kit and in large-scale fast detection of 25-hydroxyvitamin D.

BRIEF DESCRIPTION OF DRAWINGS

✳ 25-hydroxyvitamin D in the sample ● magnetic sphere ✺ other components in the sample
☆ 25-hydroxyvitamin D antibody
✦ 25-hydroxyvitamin D antigen derivative labeled with ABEI ✵ magnetic sphere coated by 25-hydroxy vitamin D antibody

✳ 25-hydroxyvitamin D in the sample ● magnetic sphere ✺ other components in the sample
☆ 25-hydroxyvitamin D antibody
✶ 25-hydroxyvitamin D antibody labeled with ABEI
✷ magnetic sphere coated by 25-hydroxy vitamin D antigen derivative

DETAILED DESCRIPTION OF EMBODIMENTS

Further description of the present disclosure will be provided below with specific embodiments. However, it should be understood that the scope of the present disclosure is not limited thereto.

Example 1 Preparation of 25-hydroxyvitamin D Detection Agent M 1.1) Formation of a Conjugate of 25-Hydroxyvitamin D Antigen Derivative and a Protein Carrier 1 mg 25-hydroxyvitamin D antigen derivative M' (formula (I) wherein m=0, n=4), 0.262 mg succinic anhydride, and 0.37 µL triethylamine (catalyst) were dissolved in anhydrous DMF and reacted at room temperature in the dark for 4 h under an argon atmosphere. 0.25 mg NHS and 1.3 mg DCC were then added and allowed to stand overnight at room temperature in the dark under argon. Then, the resulting solution was slowly dripped into bovine γ-globulin (20 mg bovine γ-globulin dissolved in 2 ml 0.1 mol/L $NaHCO_3$) solution, which was allowed to react while being stirred at room temperature for 4 h. The precipitate was removed by centrifugation, while the supernatant was purified with a G25 gel column. The protein peaks were collected (eluent: 0.1 mol/L phosphate buffered saline (PBS), pH 7.4) to obtain the conjugate of 25-hydroxyvitamin D antigen derivative M' with the protein carrier.

1.2) Activation of Magnetic Spheres

To an amount of magnetic sphere (Estapor carboxylated microspheres M1-180/20 manufactured by Merck) nano-magnetic spheres, 0.5 mg DCC per mg magnetic spheres was added, followed by the addition of DMF solution to reach a concentration of 20 mg/ml magnetic spheres, and placed in a water bath of 38° C. while being shaken or mechanically stirred for 2 hours.

1.3) Coating of the Magnetic Spheres

The supernatant was removed from the solution containing the activated nano-magnetic spheres obtained from the step 1.2), followed by the addition of carbonate buffer with pH 9.5, to reach a concentration of 20 mg/ml (of nano-magnetic spheres). To the solution, 10 µg of the conjugate formed by the 25-hydroxyvitamin D antigen derivative and the protein carrier per mg magnetic spheres was added, and then reacted while being shaken at room temperature for 2 hours. Magnetic separation was performed before the solids were washed three times with washing buffer (0.5% BSA solution) to obtain magnetic spheres well-coated by the conjugate formed by the 25-hydroxyvitamin D antigen derivative and the protein carrier, i.e., the detection agent of the present disclosure. The detecting agent obtained was then added to a diluent (carbonate buffer, phosphate buffer, borate buffer, or Tris buffer) to reach a concentration of 1 mg/ml for later use.

Example 2 Detection of 25-hydroxyvitamin D

The 25-hydroxyvitamin D detection agent prepared as in Example 1 was used to test 25-hydroxyvitamin D contents in subject samples by chemiluminescence detection method.

2.1) Labeling of 25-Hydroxyvitamin D Antibody 1 mg 25-hydroxyvitamin D antibody was mixed with 0.1 mol/L carbonate buffer (pH 9.5) to a volume of 1 ml, placed in a dialysis bag, and then dialyzed in carbonate buffer (pH 9.5) for 1 hour. The dialyzed 25-hydroxyvitamin D antibody was incorporated with 100 µg ABEI-semisuccinic amide-NHS and shaken at room temperature for 1.5 hours.

A G-25 gel column was set up, eluted clean with purified water, and equilibrated by elution with PBS buffer, pH 7.4. After the G-25 gel column was equilibrated, the 25-hydroxyvitamin D antibody labeled with ABEI was loaded onto the column. Protein solution was collected at the emergence of the protein peak. The collected protein solution was combined with an equal volume of protection solution containing 5% BSA and adjusted to 0.15 µg/ml with diluent.

2.2) Chemiluminescence Detection

The detection methods were as follows: Maglumi chemiluminescence analyzer (New Industries Biomedical Engineering Co., LTD, China) was used for measurements. 100 µl sample, 50 µl displacer (e.g., ANS), and 100 µl ABEI-labeled 25-hydroxyvitamin D monoclonal antibodies were mixed and incubated for 10 minutes. 20 µl of the stock solution containing the magnetic microspheres labeled with the 25-hydroxyvitamin D antigen derivatives prepared from step 1.3) of Example 1 (i.e., the detection agent according to the present disclosure) was added, followed by incubation for 10 min. A magnetic plate was used to separate the magnetic microspheres from the reaction mixture and the supernatant was removed. 400 µl washing solution (Tris.HCl solution) was added to wash three times. Chemiluminescent excimer was added before monitoring the relative light intensity (RLU) emitted within 3 seconds. A standard curve between 25-hydroxyvitamin D concentration and the luminous signal intensity was established by detecting the luminous signal intensities of 25-hydroxyvitamin D standard solutions in different concentrations. The contents of 25-hydroxyvitamin D in the subject samples were calculated by referring to the standard curve under the same conditions.

25-hydroxyvitamin D contents in 70 different samples were detected using the process described above.

Comparative Example 1

The contents of 25-hydroxyvitamin D in the same 70 samples as in step 2.2 of Example 2 were detected using LC-MS. Linear regression was performed between the detection results of Example 2 and these of the present comparative example, as shown in FIG. 3.

Figure 3:
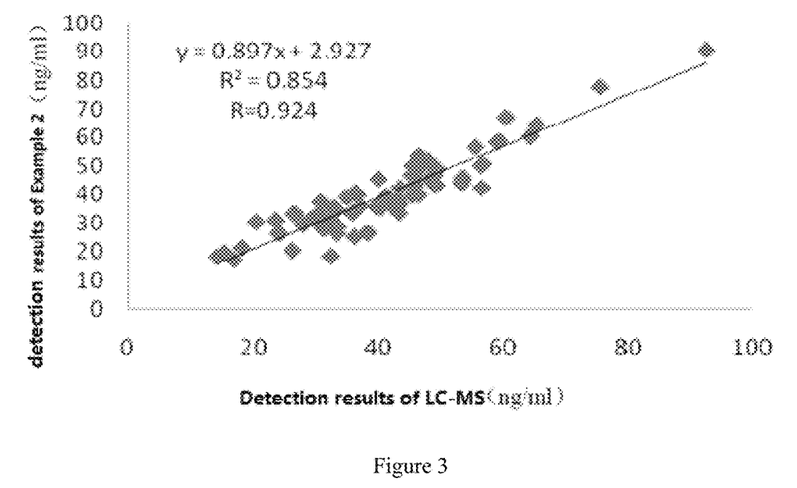
FIG. 3 shows a linear fitting of the detection results of the contents of 25-hydroxyvitamin D in 70 samples using the 25-hydroxyvitamin D detection agent according to the present disclosure and using LC-MS, respectively.

As shown in FIG. 3, the correlation coefficient between the detection results of 70 different samples obtained by using the 25-hydroxyvitamin D detection agents and the corresponding detection process thereof according to the present disclosure and the detection results obtained by LC-MS is 0.924. It indicated that the detection results obtained by the detection process according to the present disclosure were comparable to the detection results obtained by using the LC-MS equipment. In other words, the detection process according to the present disclosure can provide results with high accuracy and good specificity.

Comparative Example 2

1.1) Formation of the Conjugate of 25-Hydroxyvitamin D3 and a Protein Carrier 1 mg 25-hydroxyvitamin D3 was dissolved in 0.1 ml of anhydrous pyridine before adding 12.5 mg succinic anhydride, and reacted under argon at room temperature in the dark for 4 days. The reaction mixture was incorporated to 10 ml ethyl acetate, successively washed with water, diluted HCl, and water, dried over anhydrous sodium sulfate, and filtered. The filtrate (organic phase) was dried in vacuo to yield 25-hydroxyvitamin D3-3-hemisuccinate. 1 mg 25-hydroxyvitamin D3-3-hemisuccinate was dissolved in 0.5 ml of anhydrous dichloromethane, added with 0.28 mg NHS and 0.37 mg EDC, and stirred overnight at room temperature. The organic phase was washed with water, dried over anhydrous sodium sulfate, filtered, and the filtrate (organic phase) was dried in vacuo to yield the activated ester of 25-hydroxyvitamin D3-3-hemisuccinate. 1 mg of this activated ester was then dissolved in 100 µl DMF, which was slowly added dropwise to bovine γ-globulin solution (20 mg bovine γ-globulin dissolved in 2 ml 0.1 mol/L NaHCO$^3$). The reaction was carried out while stirring at room temperature for 4 h before centrifugation. The precipitate was removed by centrifugation while the supernatant was purified by a G25 gel column. The protein peak was collected (eluent: 0.1 mol/L phosphate buffer solution (PBS), pH 7.4) to obtain the conjugate of 25-hydroxyvitamin D3 and the protein carrier.

1.2) Activation of Magnetic Spheres

To an amount of magnetic sphere (Estapor carboxylated microspheres M1-180/20 manufactured by Merck) nano-magnetic spheres, 0.5 mg DCC per mg magnetic sphere was added, followed by the addition of DMF solution to reach a concentration of 20 mg/ml magnetic spheres, and placed in a water bath of 38° C. while being shaken or mechanically stirred for 2 hours.

1.3) Coating of the Magnetic Spheres

The supernatant was removed from the solution containing the activated nano-magnetic spheres, followed by the addition of carbonate buffer with pH 9.5, to reach a concentration of 20 mg/ml (of nano-magnetic spheres). To the solution, 10 µg of the conjugate formed by the 25-hydroxyvitamin D3 and the protein carrier per mg magnetic spheres was added, then reacted while being shaken at room temperature for 2 hours. Magnetic separation was performed before the solids were washed three times with washing buffer (0.5% BSA solution) to obtain magnetic spheres well-coated by the conjugate formed by the 25-hydroxyvitamin D3 and the protein carrier. The detecting agent obtained was then added to a diluent (carbonate buffer, phosphate buffer, borate buffer, or Tris buffer) to reach a concentration of 1 mg/ml for later use.

1.4) Chemiluminescence Detection

The same process as in Example 2 was used to test the same 70 samples, the results of which were fit with the LC-MS results in a linear regression. The correlation coefficient for the linear regression was 0.47, indicating that the accuracy of 25-hydroxyvitamin detection results obtained by using a detection agent that is prepared by coating magnetic spheres with a conjugate of natural antigen 25-hydroxyvitamin D3 as the antigen and protein carrier is much lower than that obtained by using the detection agent, prepared with the antigen derivatives, according to the present disclosure.

Example 3 Accelerated Stability Test of 25-hydroxyvitamin D Immunoassay Kit

The 25-hydroxyvitamin D immunoassay kit in the present embodiment comprises an detection agent for 25-hydroxyvitamin D prepared as in Example 1, an ABEI-labeled 25-hydroxyvitamin D monoclonal antibody, a displacer, and high calibrator and low calibrator for 25-hydroxyvitamin D.

The kit described above was applied to 25-hydroxyvitamin D sample solutions in three different concentrations (1, 2, 3) at 37° C. and the luminescence intensities in each of the three sample solutions were measured with a Maglumi chemiluminescence analyzer (New Industries Biomedical Engineering Co., LTD, China) once a day continuously for 30 days. During the entire testing process, the three 25-hydroxyvitamin D sample solutions were stored in cryopreservation while the kit used was stored at 37° C. The results are shown in FIG. 4 (1A, 2A, 3A).

Figure 4:
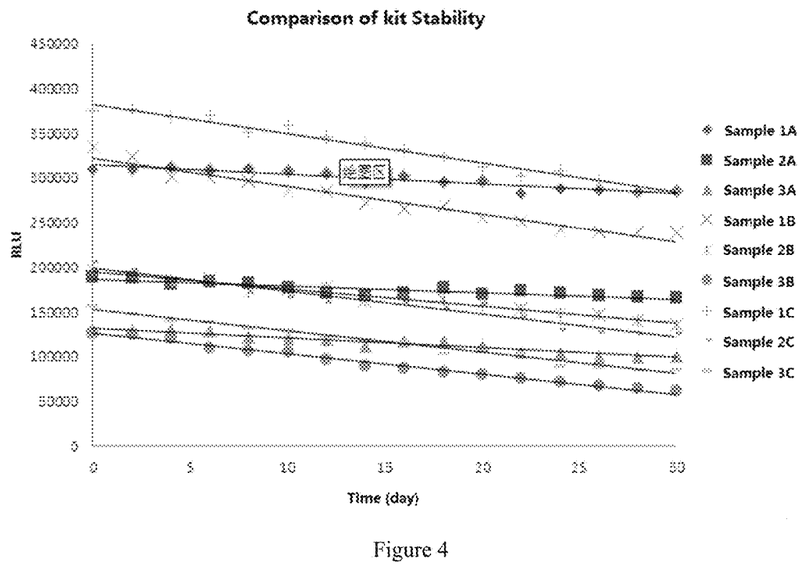
FIG. 4 shows a comparison among the test results for accelerated stability of: a 25-hydroxyvitamin D detection kit comprising the 25-hydroxyvitamin D detection agents according to the present disclosure (1A, 2A, 3A); a detection kit comprising a labeled 25-hydroxyvitamin D antigen derivative (1B, 2B, 3B); and a commercially available detection kit for 25-hydroxyvitamin D (1C, 2C, 3C).

As can be seen from FIG. 4, three samples with different concentrations of 25-hydroxyvitamin D were detected with the 25-hydroxyvitamin D assay kit of the present disclosure which was stored at 37° C. The detection results for each of the three samples were substantially consistent during the continuous measurements of 30 days. This fact fully demonstrated the good stability of the kit provided by the present disclosure, which can ensure the accuracy of detection results within a certain period of use.

Comparative Example 3

The 25-hydroxyvitamin D immunoassay kit in the present embodiment comprises an ABEI-labeled 25-hydroxyvitamin D antigen derivative prepared in this comparative example, magnetic spheres coated by 25-hydroxyvitamin D monoclonal antibody, a displacer, and high calibrator and low calibrator for 25-hydroxyvitamin D.

(1) Labeling of the 25-Hydroxyvitamin D Antigen Derivative 1 mg 25-hydroxyvitamin D antigen derivative M' (formula (I) wherein m=0, n=4) was dissolved in 100 µl DMF, followed by addition of 2.5 mg ABEI—semisuccinic amide—NHS and 10 µl triethylamine, and reacted while being stirred overnight at room temperature in the dark. The reaction product was purified by HPLC, added with an equal volume of protection solution containing 5% BSA, and diluted to 0.15 µg/ml with a diluent.

(2) Coating of Magnetic Spheres with the 25-hydroxyvitamin D Antibody

The coating process is similar to those in 1.2) and 1.3) of Example 1, except for the replacement of the conjugate of 25-hydroxyvitamin D antigen derivative and protein carrier by a 25-hydroxyvitamin D monoclonal antibody as the coating for magnetic spheres. A conjugate of the 25-dihydroxyvitamin D monoclonal antibodies and the magnetic spheres were obtained and diluted to 1 mg/ml for later use.

(3) Chemiluminescence Detection

Maglumi chemiluminescence analyzer (New Industries Biomedical Engineering Co., LTD, China) was used for measurements. 100 µl sample, 50 µl displacer (e.g., ANS), and 100 µl of the conjugate of the 25-dihydroxyvitamin D monoclonal antibodies and the magnetic spheres prepared in step (2) were mixed and incubated for 10 minutes. 400 µl washing solution (Tris-HCl solution) was added to wash for three times. 100 µl of the stock solution containing the ABEI-labeled antigen derivatives prepared in step (1) of this comparative example was added, followed by incubation for 10 min. The supernatant was removed. 400 µl washing solution (Tris-HCl solution) was added to wash for three times. Chemiluminescent excimer was added before monitoring the relative light intensity (RLU) emitted within 3 seconds. A standard curve between 25-hydroxyvitamin D concentration and the luminous signal intensity was established by detecting the luminous signal intensities of 25-hydroxyvitamin D standard solutions in different concentrations. The contents of 25-hydroxyvitamin D in the subject samples were calculated by referring to the standard curve under the same conditions.

As detected in 70 different samples (the same samples as in Example 2), a linear regression correlation coefficient of 0.858 was found between the detection results obtained by using process of this comparative example and those obtained with LC-MS (data not shown). Comparison of the results with Example 2 indicates that, when using the same antigen derivatives, the present disclosure can provide detection results with higher accuracy by modifying the antigen derivatives to provide a detection agent with improved binding specificity between the antigen derivatives and antibodies.

The accelerated stability test of the kit of this comparative example under the same conditions as Example 3 shows that the each of the three samples had significantly greater decrease in signal strength than that of Example 3 (FIG. 4, 1B, 2B, 3B). It indicates that, when using the same antigen derivatives, the present disclosure can provide a more stable assay kit by providing an detection agent with modification of the antigen derivatives, i.e., forming a conjugate with protein carrier and coating the magnetic spheres.

Comparative Example 4

Diasorin 25-hydroxyvitamin D chemiluminescent immunoassay kit (Product code: 310600) was used to detect the same three samples under the same environment as in Example 3 continuously for 30 days (the kit was also stored at 37° C. during the experiment period). The results are shown in FIG. 4 (1C, 2C, 20 3C).

As can be seen from FIG. 4, the detection results measured with the Diasorin 25-hydroxyvitamin D chemiluminescent immunoassay kit varied significantly in 30 days, indicating the poor stability of Diasorin 25-hydroxyvitamin D chemiluminescent immunoassay kit while the kit according to Example 3 of the present disclosure had significantly better results than that of Comparative Example 4.

It can be readily appreciated that the detection results from instable detection agents may become inaccurate, failing to reveal the true values, due to potential deterioration detection.

Example 4 Preparation and Characterization of 25-Hydroxyvitamin D Detection Agent N 1.1) Formation of a Conjugate of 25-hydroxyvitamin D Antigen Derivative and a Protein Carrier 1 mg 25-hydroxyvitamin D antigen derivative N' (the formula (I), wherein m=2, n=2) was dissolved in 0.1 ml DMF, added to bovine γ-globulin solution (20 mg bovine γ-globulin dissolved 2 ml 0.1 mol/L carbonate buffer), followed by addition of 25% glutaraldehyde solution to give a final concentration of 0.5% glutaraldehyde by weight. The reaction took place while being stirred at room temperature for 2 h. The precipitate was removed by centrifugation while the supernatant was purified by a G25 gel column. The protein peak was collected (eluent: 0.1 mol/L phosphate buffer solution (PBS), pH 7.4) to obtain the conjugate of the 25-hydroxyvitamin D antigen derivative N' and the protein carrier.

1.2) Coating of the Magnetic Spheres

An amount of magnetic sphere (Estapor carboxylated microspheres M1-180/20 produced by Merck) nano-magnetic spheres were dispersed in phosphate buffer with pH 7.0 (20 mg/ml), followed by addition of 10 µg of the conjugate of the 25-hydroxyvitamin D antigen derivative N' and the protein carrier prepared in step 1.1) of the present embodiment per mg of the magnetic spheres. EDC was added up to a final concentration of 10 mg/ml. The reaction took place at 40° C. under shaking for 2 hours. Magnetic separation was performed before the solids were washed three times with washing buffer (0.5% BSA solution) to obtain magnetic spheres well-coated by the conjugate of the 25-hydroxyvitamin D antigen derivative N' and the protein carrier, i.e., the detection agent of the present disclosure. The detecting agent obtained was then added to a diluent (carbonate buffer, phosphate buffer, borate buffer, or Tris buffer) to reach a concentration of 1 mg/ml for later use.

1.3) Chemiluminescence Detection of 25-hydroxyvitamin D 70 different samples were detected for their 25-hydroxyvitamin D contents by using the detection agent prepared in step 1.2) of the present embodiment and the process of Example 2. The detection results were compared with the results from the same 70 samples obtained by using LC-MS. The correlation coefficient of their linear regression was 0.917, indicating that the detection results obtained using the detection agents of the present embodiment was very close to those on the same samples obtained with LC-MS. Therefore, it further confirms the high accuracy of the detection process provided in the present embodiment.

1.4) Accelerated Stability Test of the Kit

The 25-hydroxyvitamin D immunoassay kit in the present embodiment comprises a 25-hydroxyvitamin D detection agent prepared in step 1.2) of the present embodiment, an ABEI-labeled 25-hydroxyvitamin D monoclonal antibody, a displacer, and high calibrator and low calibrator for 25-hydroxyvitamin D.

Referring to the assay procedure of the accelerated stability test of Example 3. The accelerated stability performance of the 25-hydroxyvitamin D immunoassay kit at 37° C. in 30 days was determined to be comparable to the results of Example 3. That is, the 25-hydroxyvitamin D immunological assay kit provided herein provided substantially consistent detection results for each of three samples in different concentrations in 30-day continuous measurements. This result indicates that the 25-hydroxyvitamin D immunological test kit provided in the present embodiment has good stability.

Example 5 Preparation and Characterization of 25-hydroxyvitamin D Detection Agent O 1.1) Formation of a Conjugate of 25-hydroxyvitamin D Antigen Derivative and a Protein Carrier 1 mg 25-hydroxyvitamin D derivative antigen O' (the formula (I), whereas m=1, n=6) was dissolved in 0.1 ml of anhydrous methanol, added with 1.5 mg N,N'-disuccinimidyl carbonate, and reacted under stirring at room temperature for 2 h. The product was purified by thin-layer chromatography (TLC) to give an activated derivative. 1 mg of the derivative was dissolved in DMF and added to bovine γ-globulin solution (20 mg bovine γ-globulin dissolved in 2 ml 0.1 mol/L carbonate buffer) for reaction under stirring at room temperature for 2 h. The precipitate was removed by centrifugation while the supernatant was purified by a G25 gel column. The protein peak was collected (eluent: 0.1 mol/L phosphate buffer solution (PBS), pH 7.4) to obtain the conjugate of the 25-hydroxyvitamin D antigen derivative O' and the protein carrier.

1.2) Coating of the Magnetic Spheres

Refer to Example 4 for the process of preparing the detection agent of the present embodiment, except that the conjugate was replaced by the conjugate of the 25-hydroxyvitamin D antigen derivative O' and the protein carrier of the present embodiment.

1.3) Chemiluminescence Detection of 25-hydroxyvitamin D 70 different samples were tested for their 25-hydroxyvitamin D contents by using the detection agent prepared in step 1.2) of the present embodiment and the process of Example 2. The detection results were compared with the results from the same 70 samples obtained by using LC-MS. The correlation coefficient of their linear regression was 0.921, indicating that the detection results obtained using the detection agents of the present embodiment was very close to those on the same samples obtained with LC-MS. Therefore, it further confirms the high accuracy of the assay process provided in the present embodiment.

1.4) Accelerated Stability Test of the Kit

The 25-hydroxyvitamin D immunoassay kit in the present embodiment comprises a 25-hydroxyvitamin D detection agent prepared in step 1.2) of the present embodiment, an ABEI-labeled 25-hydroxyvitamin D monoclonal antibody, a displacer, and high calibrator and low calibrator for 25-hydroxyvitamin D.

Referring to the assay procedure of the accelerated stability test of Example 3, the accelerated stability performance of the 25-hydroxyvitamin D immunoassay kit at 37° C. in 30 days was determined to be comparable to the results of Example 3. That is, the 25-hydroxyvitamin D immunological assay kit provided herein provided substantially consistent detection results for each of three samples in different concentrations in 30-day continuous measurements. This result indicates that the 25-hydroxyvitamin D immunological test kit provided in the present embodiment has good stability.

The description above has provided specific details of the present disclosure. However, a person skilled in the art can readily appreciate modifications of the embodiments disclosed herein without deviating from the spirit and scope of the present disclosure. It should also be noted that the respective aspects, various components of different embodiments, and numerous technical features recited herein can be in combined or interchanged in part or in whole. In the embodiment above, each particular embodiment referring to another can be suitably combined with any other embodiments, which could be appreciated by a person skilled in the art. Finally, a person skilled in the art can comprehend that the description above is only for the purpose of illustration by way of example, without limiting the present disclosure in any aspect.

What is claimed is:

1. A detection agent for detecting 25-hydroxyvitamin D, the detection agent comprising a magnetic sphere coated with a conjugate, wherein the conjugate comprises a 25-hydroxyvitamin D antigen derivative and a protein carrier, and wherein the 25-hydroxyvitamin D antigen derivative has the following formula:

wherein m is 0, 1, 2, or 3, and n is 2, 3, 4, 5, or 6.

2. The detection agent of claim 1, wherein the protein carrier is one or more selected from the group consisting of bovine serum albumin, cationic bovine serum albumin, hemocyanin, ovalbumin, serum albumin, bovine γ globulin, and human γ-globulin.

3. The detection agent of claim 1, wherein the magnetic sphere has on its surface one or more moieties selected from the group consisting of an epoxy group, a sulfonyl group, a carboxyl group, an amino group, an aldehyde group, an amide group, a mercapto group, and a hydroxyl group.

4. The detection agent of claim 1, wherein the size of the magnetic sphere is 0.8-3.0 μm.

5. A process for preparing the detection agent of claim 1 for detecting 25-hydroxyvitamin D comprising: coating a magnetic sphere with the conjugate of claim 1 comprising the 25-hydroxyvitamin D antigen derivative and the protein carrier.

6. The process of claim 5, wherein the coating of the magnetic sphere comprises:
    activating the magnetic sphere with a first activator before coating the magnetic sphere;
    dispersing the activated magnetic sphere into a buffer solution;
    adding the conjugate comprising the 25-hydroxyvitamin D antigen derivative and the protein carrier into the buffer solution having the dispersed activated magnetic sphere and allowing reaction of the dispersed activated magnetic spheres with the protein carrier of the conjugate to coat the activated magnetic spheres with the conjugate; and
    separating the coated activated magnetic spheres from the buffer solution, and washing the separated coated activated magnetic spheres to obtain the magnetic spheres coated with the conjugate of claim 1 comprising the 25-hydroxyvitamin D antigen derivative and a the protein carrier;

wherein the first activator is at least one of N,N-dicyclohexyl carbodiimide and 1-(3-dimethylaminopropyl)-3-ethylcarbodiimide hydrochloride or a mixture of at least one of N,N-dicyclohexyl carbodiimide and 1-(3-dimethylaminopropyl)-3-ethylcarbodiimide hydrochloride with at least one of N-hydroxysuccinimide and N-Hydroxysulfosuccinimide sodium salt.

7. The process of claim 5, further comprising a step of preparing the conjugate comprising the 25-hydroxyvitamin D antigen derivative and the protein carrier, the step comprises allowing the 25-hydroxyvitamin D antigen derivative and the protein carrier to go through a coupling reaction in the presence of a coupling agent and a solvent to yield the conjugate; wherein the coupling agent is at least one selected from the group consisting of glutaraldehyde and N,N'-disuccinimidyl carbonate; and the solvent is at least one selected from the group consisting of dimethylformamide, dimethylsulfoxide, acetone, and chloroform.

8. The process of claim 5, further comprising a step of preparing the conjugate comprising the 25-hydroxyvitamin antigen derivative and the protein carrier, which comprises:
providing the 25-hydroxyvitamin D antigen derivative with a carboxyl group and activating the carboxyl group with a second activator to provide an activated 25-hydroxyvitamin D; and
coupling the activated 25-hydroxyvitamin D antigen derivative with the protein carrier in the presence of a solvent to provide the conjugate and
separating the conjugate;
wherein the second activator is a mixture of at least one of N-hydroxysuccinimide and N-hydroxysuccinimide sodium salt with at least one of N,N-dicyclohexyl carbodiimide and 1-(3-dimethylaminopropyl)-3-ethylcarbodiimide hydrochloride; and the solvent is at least one selected from the group consisting of dimethylformamide, dimethylsulfoxide, acetone, and chloroform.

9. The process of claim 5, wherein a molar ratio of the 25-hydroxyvitamin D antigen derivative to the protein carrier in the detection agent is 10:1 to 20:1.

10. A process of immunoassay for detecting 25-hydroxyvitamin D, comprising:
allowing 25-hydroxyvitamin D in a subject sample and the detection agent of claim 1 to competitively bind with a 25-hydroxyvitamin D antibody wherein the 25-hydroxyvitamin antibody is conjugated with a label; and
detecting the 25-hydroxyvitamin D antibody bound with the detection agent.

11. The process of claim 10, wherein the label is selected from the group consisting of a fluorescent label, a luminescent label, a biotin label, a gold label, and an enzymatic label.

12. The process of claim 10, comprising:
a. incubating a subject sample with a 25-hydroxyvitamin D antibody wherein the 25-hydroxyvitamin D antibody is conjugated with a luminescent label;
b. incorporating the mixture obtained from step a with the detection agent of claim 1, so that 25-hydroxyvitamin D in a subject sample and the detection agent competitively bind to the 25-hydroxyvitamin D antibody to form a complex;
c. performing magnetic separation to obtain the complex comprising the 25-hydroxyvitamin D antibody bound with the detection agent;
d. adding an excitation substrate to the conjugate obtained from step c to generate a luminescent signal; and
e. calculating an amount of the 25-hydroxyvitamin D in the subject sample according to the intensity of the luminescent signal detected in step d.

13. An immunoassay kit for detection of 25-hydroxyvitamin D, comprising a 25-hydroxyvitamin D antibody conjugated with a label and the detection agent of claim 1.

14. The kit of claim 13, wherein the label is selected from the group consisting of a fluorescent label, a luminescent label, a biotin label, a gold label, and an enzymatic label.

15. The process of claim 5, wherein the protein carrier is one or more selected from the group consisting of bovine serum albumin, cationic bovine serum albumin, hemocyanin, ovalbumin, serum albumin, bovine γ globulin, and human γ-globulin.

16. The process of claim 5, wherein the magnetic sphere has on its surface one or more moieties selected from the group consisting of an epoxy group, a sulfonyl group, a carboxyl group, an amino group, an aldehyde group, an amide group, a mercapto group, and a hydroxyl group.

17. The process of claim 5, wherein the size of the magnetic sphere is 0.8-3.0 μm.

18. The kit of claim 13, wherein the protein carrier is one or more selected from the group consisting of bovine serum albumin, cationic bovine serum albumin, hemocyanin, ovalbumin, serum albumin, bovine γ globulin, and human γ-globulin.

19. The kit of claim 13, wherein the magnetic sphere has on its surface one or more moieties selected from the group consisting of an epoxy group, a sulfonyl group, a carboxyl group, an amino group, an aldehyde group, an amide group, a mercapto group, and a hydroxyl group.

20. The kit of claim 13, wherein the size at the magnetic sphere is 0.8-3.0 μm.

* * * * *